United States Patent [19]
Gaylord, Jr.

[11] 3,970,079
[45] July 20, 1976

[54] BODY SUPPORT BINDER AND METHOD OF FABRICATING SAME

[75] Inventor: John F. Gaylord, Jr., Matthews, N.C.

[73] Assignee: Medical Specialties, Inc., Charlotte, N.C.

[22] Filed: Mar. 21, 1975

[21] Appl. No.: 560,641

[52] U.S. Cl. .................... 128/78; 128/541; 156/157
[51] Int. Cl.² .......................................... A61F 5/02
[58] Field of Search ............. 128/78, 87, 541, 579, 128/DIG. 15; 2/DIG. 7; 156/304, 306, 309, 157, 93

[56] References Cited
UNITED STATES PATENTS

| | | | |
|---|---|---|---|
| 2,372,632 | 3/1945 | Webb | 156/93 X |
| 2,412,693 | 12/1946 | Pierson | 156/157 |
| 3,122,465 | 2/1964 | Keller et al. | 156/93 |
| 3,134,703 | 5/1964 | Listner | 156/157 |
| 3,561,436 | 2/1971 | Gaylord, Jr. | 128/87 |
| 3,659,843 | 5/1972 | Kojigian, Jr. | 128/DIG. 15 |

*Primary Examiner*—John D. Yasko
*Attorney, Agent, or Firm*—Bell, Seltzer, Park & Gibson

[57] ABSTRACT

An elongate body support binder and method of fabricating the same. The binder comprises serially arranged fabric panels, and a joint structure for interconnecting the adjacent ends of the panels and which includes a plastic strip having substantial resistance to lateral bending to thereby resist rolling of the longitudinal side edges of the binder when in use.

16 Claims, 13 Drawing Figures

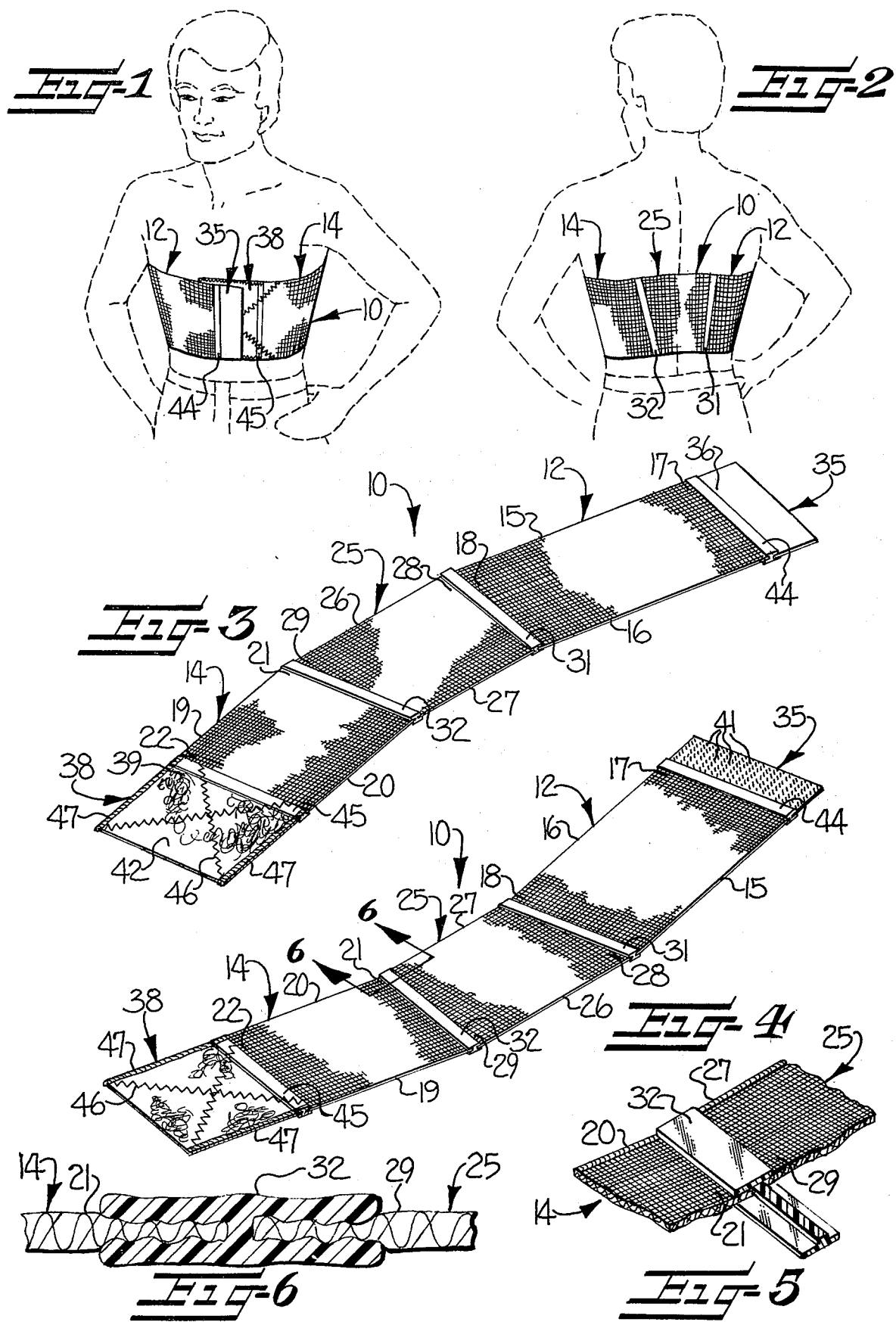

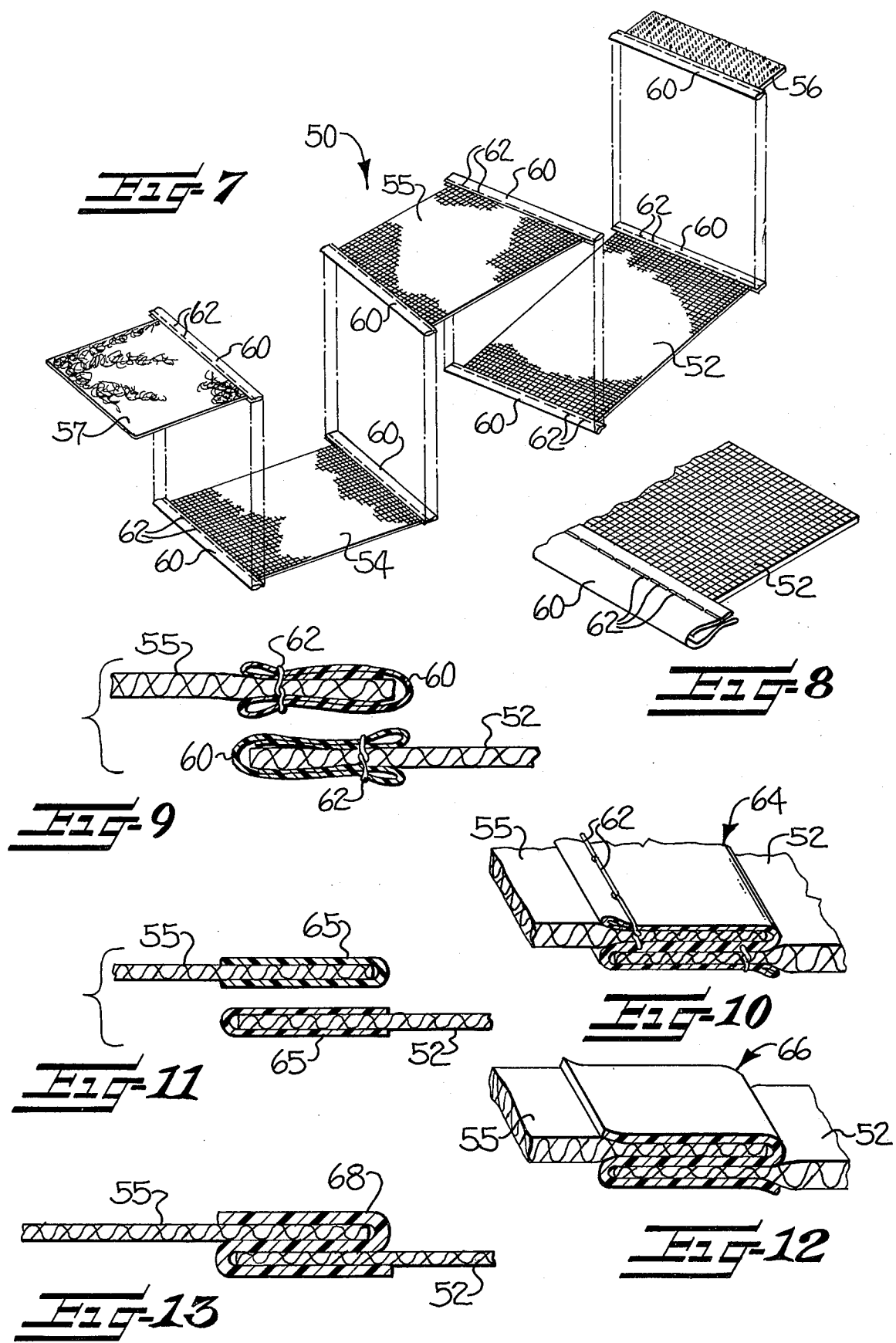

BODY SUPPORT BINDER AND METHOD OF FABRICATING SAME

The present invention relates to an elongate body support binder adapted to encircle and reinforce a portion of the body of a wearer and characterized by the ability to resist rolling of the longitudinal side edges when in use without employing separate stiffeners or the like.

In applicant's prior U.S. Pat. No. 3,561,436, there is disclosed a thoracic binder for encircling and reinforcing the thorax of a wearer, and which includes a plurality of serially arranged panels which are interconnected by stitching. In the prior patent to Kaplan, U.S. Pat. No. 3,752,163, there is disclosed a relatively wide body support binder which is fabricated from a plurality of fabric panels, the panels again being serially arranged and interconnected by stitching.

In binders or supports of the above general type, difficulties are often encountered in that the longitudinal side edges of the binder roll upon themselves after the binder has been worn for a period of time. As will be apparent, such rolled edges tend to bite into the body and can result in considerable discomfort. Also, the rolled edges create unsightly bulges which may be visible through the outer clothing of the wearer.

It is accordingly an object of the present invention to provide an elongate body support binder which is adapted to provide firm body support, and which effectively resists rolling of the longitudinal side edges and thereby avoids the above noted problems.

It is another object of the present invention to provide an elongate body support binder which resists rolling of the longitudinal side edges without employing separate metal or plastic stiffeners, stays, or the like, and which also eliminates the need for forming tucks or pockets to accommodate such stiffeners or stays.

It is a more particular object of the present invention to provide an elongate body support binder of the described type and wherein the adjacent panels are joined by a strip of plastic material which serves not only to join the panels, but also to provide sufficient rsistance to lateral bending to effectively prevent the rolling of the side edges of the panels during use.

Some of the objects and advantages of the invention having been stated, other objects will appear as the description proceeds, when taken in connection with the accompanying drawings, in which FIG. 1 is a front elevation view of a body support binder embodying the present invention and shown as being worn about a patient's thorax;

FIG. 2 is a rear elevation view of the body support binder as worn by a patient;

FIG. 3 is an enlarged perspective view looking at the outside surface of the body support binder;

FIG. 4 is a perspective view similar to FIG. 3 but looking at the inside surface of the binder;

FIG. 5 is a fragmentary perspective view, partly broken away, and illustrating the strip of plastic material for joining the adjacent ends of the adjacent panels;

FIG. 6 is an enlarged cross-sectional view taken substantially along the line 6—6 of FIG. 4;

FIG. 7 is an exploded perspective view of another embodiment of a body support binder embodying the present invention and illustrating the manner in which the several panels are interconnected;

FIG. 8 is an enlarged fragmentary perspective view illustrating the end of one fabric panel and the strip of plastic material secured thereto;

FIG. 9 is an enlarged cross-sectional view of two ends of adjacent panels and illustrating the manner in which they are overlapped prior to being interconnected;

FIG. 10 is a sectioned perspective view illustrating the ends shown in FIG. 9 after being interconnected;

FIG. 11 is a view similar to FIG. 9 but illustrating another embodiment of a strip of plastic material which may be employed with the present invention;

FIG. 12 is a sectioned perspective view illustrating the ends shown in FIG. 11 after being interconnected; and FIG. 13 is a view similar to FIGS. 9 and 11, and illustrates still another embodiment of a plastic strip which may be used with the present invention.

Referring more specifically to the drawings, FIGS. 1–6 illustrate an improved body support binder 10 in the form of a thoracic belt which embodies the present invention. The binder 10 comprises first and second elongate end panels 12 and 14 of similar rectangular configuration, the panel 12 having opposing sides 15, 16 and opposing ends 17, 18, and the panel 14 having opposiing sides 19, 20 and opposing ends 21, 22.

An intermediate panel 25 is positioned between the two end panels, the panel 25 being of isosceles trapezoidal configuration. More particularly, the panel 25 has opposing parallel sides 26, 27, and opposing non-parallel ends 28, 29. The end 28 is positioned in adjacent end to end relationship with respect to the end 18 of the adjacent end panel 12, and the end 29 is similarly positioned with respect to the end 21 of the panel 14. Thus the panels may be said to be arranged serially in end to end relationship to define an elongate binder having sufficient length to encircle the thorax of a wearer as seen in FIGS. 1 and 2.

The panels 12 and 14 are each of about the same width as the length of the edges at the ends 28 and 29 of the panel 25, and the side edges 15, 16 and 19, 20 each extend substantially perpendicular to the adjacent end 28, 29, respectively. By this arrangement, the binder assumes a somewhat arcuate configuration for the purposes set forth below. The three panels 12, 14, and 25 are joined together in the indicated end to end relationship by strips 31 and 32 of plastic material. In particular, the strip 31 extends along the length of the adjacent ends 18 and 28, and the strip 32 extends along the length of the adjacent ends 21 and 29. The strips 31 and 32 each have an H-shaped cross-sectional configuration to define oppositely facing channels, with the adjacent ends of the panels being received and secured within the channels in co-planar relationship, note FIGS. 5 and 6. The strips may be formed by a conventional extrusion process, and may comprise any of a number of suitable thermoplastic materials, such as polyvinyl chloride. Surprisingly, it has been found that the strips not only serve to join the panels, but they also provide sufficient resistance to lateral bending to thereby effectively prevent rolling of the side edges of the panels when the binder is positioned about the body member of the wearer.

The binder 10 further comprises fastening means for releasably interconnecting the distal ends of the binder in overlapping relationship when positioned about the body member. As illustrated, the fastening means incorporates a conventional "Velcro" type fastener, and comprises a first outer panel 35 having an inner end 36 positioned in end to end relationship with respect to the distal end 17 of the panel 12, and a second outer panel 38 having an inner end 39 positioned in end to end relationship with respect to the distal end 22 of the panel 14. One face of the panel 35 mounts a plurality of hook-shaped fiber members 41, and the opposite face of the panel 38 incorporates a loose fibrous material 42. The hook-shaped fiber members 41 are adapted to releasably engage the fibrous material 42 in a manner well known in the art, note for example U.S. Pat. No. 2,717,437.

The outer panel 35 is joined to the end 17 of the panel 12 by a strip 44 of plastic material, and the panel 38 is similarly joined to the end 22 of the panel 14 by means of the strip 45. The strips 44 and 45 are of the same construction and configuration as the above described strips 31 and 32, and they interconnect the adjacent panels in the manner described above. To secure the fibrous material 42 to the panel 38, there may also be provided lines of crossed stitching indicated at 46, and an over-edge stitching indicated at 47.

The panels 12, 14 and 25 may comprise a conventional elastic woven textile fabric or the like, with the elastic strands extending in the longitudinal or body encircling direction. In a preferred embodiment, the fabric comprises 65% cotten fibers, 25% rayon, and 10% rubber. When worn, the binder may be slightly stretched so that it is tightly placed about the body member of the wearer. For example, when the binder is positioned about the thorax as shown in FIGS. 1 and 2, the longer of the two longitudinal side edges is positioned above the opposite side edge, with the intermediate panel 25 located in the middle of the wearer's back. The second panel 14 is held against the chest of the wearer, and the first end panel 12 is then pulled tightly into overlapping relationship with respect to the outer panel 38, whereupon the hook-shaped fiber members 41 on the panel 35 are pressed into surface contact with the fibrous material 42 on the panel 38 to thereby firmly secure the binder about the thorax of the wearer. In this regard, it will be noted that the arcuate configuration of the binder results in a natural somewhat tapered configuration when it is placed about the thorax of the wearer so as to conform more readily to the shape of that portion of the wearer's body.

To fabricate the binder 10, the panels 12, 14, 25, 35, and 38 are initially cut from suitable supply rolls of the fabric, and the ends thereof are then interconnected to form the configuration described above. More particularly, each pair of adjacent ends of the panels are positioned within the channels of the associated H-shaped strip of plastic material, and the strip is then heated and compressed by any suitable arrangement, such as dielectric heating, to compress the strip and secure the ends therewithin. The strips are initially dimensioned to freely receive the ends of the fabric panels within the channels, and typically, the strips have an initial overall transverse thickness of between about 0.08 and 0.09 inches, a gap width in the channels of between about 0.05 to 0.06 inches, and a length of between about one half to five eights inches in the body encircling direction. The transverse central leg of the H-shaped strip has a width of between about 0.014 to 0.04 inches. After heating and compression, the H-shaped strip typically has a transverse width of about 0.03 inches, with the plastic being partially embedded within the interstices of the fabric panels to secure the same within the channels, note FIG. 6.

Another embodiment of a binder which incorporates the present invention is indicated generally at 50 in FIGS. 7–10. As illustrated, the binder 50 comprises rectangular end panels 52 and 54, an intermediate panel 55 of isosceles trapezoidal configuration, and outer panels 56 and 57 which mount the "Velcro" fastening means. These various panels are initially cut to the desired length, and each end thereof is then covered with a segment 60 of thin plastic film. More particularly, each film segment 60 is folded upon itself to form a U-shaped cross-sectional configuration, and the folded segment is then slipped over the end of the associated panel such that a doubled layer of the segment is positioned over both the top and bottom faces of the panel, note FIGS. 8 and 9. To secure the segments in this position, the segments and panels are stitched together as indicated at 62.

The adjacent ends of the adjacent panels and associated film segments 60 are then positioned in overlapping relationship as seen in FIG. 9, and then segments are then heated and pressed together to fuse the plastic layers together and thereby join the fabric panels and result in the final joining strip 64 of S-shaped cross-sectional configuration as shown in FIG. 10. In this regard, it has been found that a film segment of polyvinyl chloride plastic having a thickness of between about 4 to 6 mils provides the desired degree of resistance to lateral bending when formed into a strip 64 as seen in FIG. 10, and it effectively prevents the side edges of the binder from rolling during use.

Still another embodiment of the present invention is shown in FIGS. 11 and 12, wherein the segments 65 of plastic material initially have a U-shaped cross-sectional configuration. The open channel formed by each segment is adapted to receive the end of one of the fabric panels, and the panels and associated segment are then positioned in overlapping relation as seen in FIG. 11. Upon heating and compression, the two segments 65 fuse together and are secured to the panels to form a plastic strip 66 of S-shaped cross-sectional configuration as seen in FIG. 12.

FIG. 13 illustrates a further embodiment of the invention wherein the panels are interconnected by a unitary strip 68 of plastic material which has an S-shaped cross-sectional configuration to define oppositely facing channels and with the adjacent ends of the panels being received within the channels. Upon heating and compression of the strip 68, it assumes a compressed configuration substantially as shown at 66 in FIG. 12 and wherein the panels are secured together.

In the drawings and specification, there has been set forth a preferred embodiment of the invention, and although specific terms are employed, they are used in a generic and descriptive sense only and not for purposes of limitation.

That which is claimed is:

1. An elongate body support binder adapted to encircle and reinforce a portion of the body of a wearer and characterized by the ability to resist rolling of the longitudinal side edges when in use without employing separate stiffeners or the like, said binder comprising a plurality of fabric panels arranged serially in adjacent end to end relationship and with the adjacent ends of the adjacent panels in substantially abutting, non-overlapping relationship to define an elongate binder having sufficient length to encircle a body member of a wearer, means joining the adjacent ends of the adjacent panels and comprising a strip of plastic material extending along the length of the adjacent ends, said strip having an H-shaped cross-sectional configuration to define oppositely facing channels and with said adjacent ends being received within said channels, said strip further having sufficient resistance to lateral bending to effectively prevent rolling of the longitudinal side edges of the panels when the binder is positioned about the body member of a wearer, and fastening means carried by the panels for releasably interconnecting the distal ends of the binder.

2. The body support binder as defined in claim 1 wherein at least one of said fabric panels comprises an elastic fiber material which is stretchable in the body encircling direction.

3. The body support binder as defined in claim 2 wherein said fastening means comprises a plurality of hook-shaped fiber members secured to one of the distal ends of the binder, and a loose, fibrous material secured to the other of the distal ends of the binder, said hook-shaped fiber members being adapted to releasably engage said fibrous material to fasten the distal ends in overlapping relationship.

4. The body support binder as defined in claim 1 wherein said strip has an overall transverse thickness of about 0.030 inches, and a length of between about one-half to five-eights inches in the body encircling direction.

5. An elongate body support binder adapted to encircle and reinforce a portion of the body of a wearer and characterized by the ability to resist rolling of the longitudinal side edges when in use without employing separate stiffeners or the like, said binder comprising first and second elongate end panels of textile fabric, each of said end panels having opposite sides and opposite ends, an intermediate panel of textile fabric positioned between said first and second end panels and having opposite sides and opposite ends, each of said ends of said intermediate panel being positioned in adjacent end to end relationship with respect to one of the ends of the adjacent end panel to thereby define an elongate binder having sufficient length to encircle a body member of a wearer, means joining the adjacent ends of the adjacent panels, said joining means comprising a first strip of plastic material extending along the length of the adjacent ends between said first end panel and said intermediate panel and being secured to being secured to each of the adjacent of the adjacent ends, and a second strip of plastic material extending along the length of the adjacent ends between said second end panel and said intermediate panel and being ends, each of said strips having a configuration which provides substantial resistance to lateral bending to effectively prevent rolling of the side edges of the panels when the binder is positioned about the body member of a wearer, and fastening means carried by said end panels for releasably interconnecting the distal ends of the binder when the binder is positioned about the body member.

6. The body support binder as defined in claim 5 wherein sid end panels are substantially rectangular, and wherein said intermediate panel is of substantially isoscles trapezoidal configuration, with said sides of said intermediate panel being parallel and said ends thereof being non-parallel.

7. The body support binder as defined in claim 6 wherein said opposite sides of said end panels each extend substantially perpendicular to the adjacent non-parallel end of said intermediate panel.

8. The body support member as defined in claim 5 wherein said fastening means comprises a first outer panel having an end positioned in end to end relationship with respect to the distal end of one of said first and second end panels, and a plurality of hook-shaped fiber members overlying one face of said first outer panel, a second outer panel having an end positioned in end to end relationship with respect to the distal end of the other of said first and second end panels, and a loose, fibrous material overlying the opposite face of said second outer panel, said hook-shaped fiber members of said first outer panel being adapted to releasably engage said fibrous material on said second outer panel, and means joining the end of said first outer panel with the adjacent distal end of said one panel, and joining the end of said second outer panel with the adjacent distal end of said other end panel.

9. The body support binder as defined in claim 8 wherein said outer panel joining means comprises a third strip of plastic material extending along the length of the adjacent ends between said one end panel and said first outer panel and being secured to each of such adjacent ends, and a fourth strip of plastic material extending along the length of the adjacent ends between said other end panel and said second outer panel and being secured to each of such adjacent ends, each of said third and fourth strips having a configuration which provides substantial resistance to lateral bending to effectively prevent rolling of the side edges of the panels when the binder is positioned about the body member of a wearer.

10. An elongate body support binder adapted to encircle and reinforce a portion of the body of a wearer and characterized by the ability to resist rolling of the longitudinal side edges when in use without employing separate stiffeners or the like, said binder comprising a plurality of fabric panels arranged serially in adjacent end to end relationship and with the adjacent ends of the adjacent panels being disposed in parallel, overlapping relationship to define an elongate binder having sufficient length to encircle a body member of a wearer, means joining the adjacent ends of the adjacent panels and comprising a strip of plastic material extending along the length of the adjacent ends, said strip having an S-shaped cross-sectional configuration to define oppositely facing channels and with said adjacent ends being received within said channels, said strip further having sufficient resistance to lateral bending to effectively prevent rolling of the longitudinal side edges of the panels when the binder is positioned about the body member of a wearer, and fastening means carried by the panels for releasably interconnecting the distal ends of the binder.

11. The body support binder as defined in claim 10 wherein said joining means further comprises stitching extending between said strip and each of the adjacent panels.

12. A method of fabricating an elongate body support binder adapted to encircle and reinforce a portion of the body of a wearer and characterized by the ability to resist rolling of the longitudinal side edges when in use without employing separate stiffeners or the like, said method comprising the steps of
arranging a plurality of fabric panels in a serial end to end relationship,
interconnecting the adjacent ends of the adjacent panels to form an elongate binder, and including positioning at least one strip of thermoplastic material along the adjacent ends of the panels, and then heating the strip while compressing the same into contact with the ends of the panels to thereby join the strip to the ends of the panels and such that the resulting thermoplastic material has substantial resistance to lateral bending to thereby increase the resistance of the panels to lateral bending and effectively prevent rolliing of the longitudinal side edges when the binder is positioned about the body member of a wearer and such that the thermoplastic material serves as the sole means for interconnecting the adjacent ends of the panels, and
securing cooperating fasteners to the distal ends of the binder such that the distal ends may be releasably interconnected upon the binder being positioned to encircle a body member of a wearer.

13. The method as defined in claim 12 wherein the step of positioning a strip of plastic material along the adjacent ends includes placing a unitary strip of plastic material so as to overlie both faces of the adjacent ends of the adjacent panels prior to the heating of the strip and such that a portion of the strip is positioned intermediate the adjacent panels.

14. A method of fabricating an elongate body support binder adapted to encircle and reinforce a portion of the body of a wearer and characterized by the ability to resist rolling of the longitudinal side edges when in use without employing separate stiffeners or the like, said method comprising the steps of
arranging a plurality of fabric panels in a serial end to end relationship,
interconnecting the adjacent ends of the adjacent panels to form an elongate binder, and including positioning a strip of thermoplastic material having a U-shaped cross-sectional configuration to overlie the end of each of the adjacent panels and such that each end is received within the open channel defined by the associated U-shaped strip, positioning the ends of the adjacent panels and associated strips in overlapping relationship, and then heating the strips while compressing thte same together to interconnect the ends, and such that the thermoplastic material serves to increase the resistance of the panels to lateral bending and rolling of the longitudinal side edges when the binder is positioned about the body member of a wearer, and
securing cooperating fasteners to the distal ends of the binder such that the distal ends may be releasably interconnected upon the binder being positioned to encircle a body member of a wearer.

15. The method as defined in claim 14 comprising the further step of sewing each U-shaped strip to the associated end prior to positioning the ends of the adjacent panels in overlapping relationship.

16. A method of fabricating an elongate body support binder adapted to encircle and reinforce a portion of the body of a wearer and characterized by the ability to resist rolling of the longitudinal side edges when in use without employing separate stiffeners or the like, said method comprising the steps of
arranging a plurality of fabric panels in a serial end to end relationship,
interconnecting the adjacent ends of the adjacent panels to form an elongate binder, and including positioning a strip of thermoplastic material having an H-shaped cross-sectional configuration intermediate the adjacent ends and such that the ends are substantially co-planar with each end being received within one of the channels defined by the H-shaped strip, and then heating the strip while compressing the same to join the strip to each of the adjacent ends, and such that the strip serves to increase the resistance of the panels to lateral bending and rolling of the longitudinal side edges when the binder is positioned about the body member of a wearer, and
securing cooperating fasteners to the distal ends of the binder such that the distal ends may be releasably interconnected upon the binder being positioned to encircle a body member of a wearer.

* * * * *

UNITED STATES PATENT AND TRADEMARK OFFICE
CERTIFICATE OF CORRECTION

PATENT NO. : 3,970,079
DATED : July 20, 1976
INVENTOR(S) : John F. Gaylord, Jr.

It is certified that error appears in the above-identified patent and that said Letters Patent are hereby corrected as shown below:

Column 4, Line 20, "then" should be --the--;

Column 5, Line 51, delete "being", second occurrence;

Column 5, Line 52, delete "secured to" and "of the adjacent", second occurrence;

Column 5, line 66, "sid" should be --said--;

Column 5, Line 68, "isoscles" should be --isosceles--;

Column 6, Line 23, after "one" insert --end--; and

Column 8, Line 6, "thte" should be --the--.

Signed and Sealed this

Twenty-sixth Day of October 1976

[SEAL]

Attest:

RUTH C. MASON
Attesting Officer

C. MARSHALL DANN
Commissioner of Patents and Trademarks